(12) United States Patent
Murashita (10) Patent No.: US 7,981,037 B2
(45) Date of Patent: Jul. 19, 2011

(54) ULTRASOUND DIAGNOSIS APPARATUS

(75) Inventor: Masaru Murashita, Mitaka (JP)

(73) Assignee: Aloka Co., Ltd., Tokyo (JP)

(*) Notice: Subject to any disclaimer, the term of this patent is extended or adjusted under 35 U.S.C. 154(b) by 535 days.

(21) Appl. No.: 11/822,101

(22) Filed: Jul. 2, 2007

(65) Prior Publication Data
US 2008/0009735 A1    Jan. 10, 2008

(30) Foreign Application Priority Data
Jul. 5, 2006    (JP) .................................. 2006-185650

(51) Int. Cl.
*A61B 8/00*    (2006.01)

(52) U.S. Cl. ........................................ 600/443; 600/450

(58) Field of Classification Search ........... 600/437–455
See application file for complete search history.

(56) References Cited

U.S. PATENT DOCUMENTS

| | | | | |
|---|---|---|---|---|
| 5,322,067 A * | 6/1994 | Prater et al. | ................... | 600/443 |
| 5,409,010 A * | 4/1995 | Beach et al. | ................... | 600/455 |
| 5,465,721 A * | 11/1995 | Kishimoto et al. | ........... | 600/443 |
| 5,515,849 A | 5/1996 | Murashita et al. | | |
| 6,135,959 A * | 10/2000 | Murashita et al. | ............ | 600/443 |
| 2001/0024516 A1 | 9/2001 | Yoshioka et al. | | |
| 2004/0097808 A1 | 5/2004 | Murashita | | |
| 2005/0049503 A1* | 3/2005 | Schoisswohl et al. | ........ | 600/453 |
| 2006/0074315 A1* | 4/2006 | Liang et al. | ................... | 600/450 |

FOREIGN PATENT DOCUMENTS

| | | |
|---|---|---|
| JP | 7-23944 A | 1/1995 |
| JP | 7-222742 A | 8/1995 |
| JP | 7-241290 A | 9/1995 |
| JP | 8-103442 A | 4/1996 |
| JP | 8-173417 A | 7/1996 |
| JP | 9-253085 A | 9/1997 |
| JP | 10-99328 A | 4/1998 |
| JP | 10-504225 A | 4/1998 |
| JP | 11-221210 A | 8/1999 |
| JP | 11221210 | 8/1999 |
| JP | 3045642 B2 | 5/2000 |
| JP | 2000-197633 A | 7/2000 |
| JP | 2001-87268 A | 4/2001 |
| JP | 2004-159997 A | 6/2004 |
| WO | WO 96/41312 A1 | 12/1996 |

OTHER PUBLICATIONS

Thomas R. Nelson, et al., "Three-Dimensional Echocardiographic Evaluation of Fetal Heart Anatomy and Function: Acquisition, analysis, and Display", Journal of Ultrasound in Medicine, vol. 15, No. 1, pp. 1-9, 1996.
European Office Action dated Oct. 31, 2007, Application No. 07012520.8-1265.
Japanese Office Action dated Jun. 24, 2008, issued in corresponding Japanese Patent Application No. 2006-185650.

* cited by examiner

*Primary Examiner* — Sanjay Cattungal
(74) *Attorney, Agent, or Firm* — Westerman, Hattori, Daniels & Adrian, LLP (57) ABSTRACT

An ultrasound diagnosis apparatus which performs ultrasonic diagnosis with respect of a fetal heart. An area change measurement section calculates an area of a specific heart chamber (left ventricle) in the fetal heart in frame units. Further, the area change measurement section generates a graph representing the area which is calculated in frame units. The maximum value and the minimum value are specified in the graph to thereby specify end-diastole and end-systole. Based on this information, a heart rate and a cardiac cycle with regard to the fetal heart are calculated. Further, an ejection fraction is also calculated from an end-diastolic area and an end-systolic area.

9 Claims, 9 Drawing Sheets

ULTRASOUND DIAGNOSIS APPARATUS

BACKGROUND

1. Technical Field

The present invention relates to an ultrasound diagnosis apparatus, and more particularly to ultrasonic diagnosis technology for a fetal heart.

2. Related Art

Ultrasonic diagnosis of a fetus in it's mother womb has become commonplace in medical practice. One of the purposes of such diagnoses is to diagnose or treat congenital heart diseases at an early stage. If a serious heart disease can be diagnosed prior to delivery, it is often possible to successfully treat the disease using medicine, surgery, or the like immediately after childbirth. In ultrasonic diagnosis of a fetal heart, the shape or size of the heart is displayed on a tomographic image, or the state of blood flow in the heart is displayed on a two-dimensional color Doppler image (or a color flow mapping image). Also, according to the pulse Doppler method, Doppler information obtained from a sample gate (or a sample volume) which is set within the heart is subjected to frequency analysis, so that Doppler waves formed by the frequency analysis are displayed. Alternatively, it is also possible to use three-dimensional ultrasonic diagnosis technology to perform three-dimensional image forming or three-dimensional measurement with regard to the fetal heart.

JP 3045642 B describes processing of a two-dimensional ultrasonic image, and particularly describes processing for extracting the outline of the left ventricle in the heart to form an image such as a multi-ring. JP 2004-159997 A describes processing of a three-dimensional ultrasonic image, and particularly describes processing for extracting a heart chamber portion within the heart. JP 2000-197633 A discloses measurement and analysis of a cardiac valve signal of a fetus. Although this publication, JP 2000-197633 A, describes a method which uses an ultrasonic Doppler method, the publication does not describe technology of processing an image which represents a change in the shape of the heart such as a tomographic image and a three-dimensional image to thereby obtain information indicative of the motion of the heart. JP 11-221210 A describes technology of displaying a temporal change of the areas of a plurality of regions defined in the left ventricle in a plurality of graphs. JP 8-103442 A describes image processing technology for extracting the left ventricle as a closed region. None of the above-noted publications describes the technology of obtaining information which is an alternative to electrocardiographic information from the temporal change in the shape of the heart.

Generally, in ultrasonic diagnosis of the heart, an electrocardiograph is used to measure an electrocardiographic signal in real time, and the electrocardiographic signal is then used as information representing the period of motion of the heart or as a synchronization signal for measurement. However, it is not possible to bring a plurality of electrodes into direct contact with a fetus for obtaining an electrocardiographic signal. In this regard, ultrasonic diagnosis of a fetus in the womb suffers from a specific problem which would not arise in the normal ultrasonic diagnosis of the heart. As such, with regard to fetuses, it is difficult to obtain information concerning heartbeats (cardiac information) in the ultrasonic diagnosis of the heart, which makes it difficult to recognize the state of the heart or measure the heart functions.

Here, as the cardiac cycle of the fetal heart is much shorter than that of the adult heart, it is necessary to increase the frame rate (or the volume rate) when displaying the fetal heart in an ultrasonic image. However, if data transmission and reception based on the ultrasonic Doppler method described in JP 2000-197633 A indicated above is performed in addition to data transmission and reception for measuring or displaying the fetal heart as an ultrasonic image, the frame rate (or the volume rate) is inevitably reduced.

SUMMARY

In accordance with one aspect, the present invention advantageously provides an ultrasound diagnosis apparatus suitable for diagnosis or measurement of the fetal heart.

In accordance with another aspect, the present invention advantageously provides an ultrasound diagnosis apparatus which can obtain information concerning heartbeats (cardiac information) in real time while performing ultrasonic diagnosis of the fetal heart.

In accordance with still another aspect, the present invention advantageously provides an ultrasound diagnosis apparatus which can obtain information representing the periodical motion of the heart based on echo data which is used for representing fetal heart in an image.

The present invention relates to an ultrasound diagnosis apparatus which includes a transmitter/receiver section for transmitting and receiving ultrasound with respect to a fetal heart; a motion information measurement section for measuring motion information representing a temporal change in a shape of the heart caused by a periodical motion of the fetal heart, based on data obtained by transmission and reception of the ultrasound; and a time measurement section for measuring a specific time in the periodical motion of the fetal heart based on the motion information.

With the above structure, ultrasound is transmitted to and received from a fetus in the mother womb. Consequently, echo data for representing the fetal heart in a two-dimensional image or a three-dimensional image is captured. In general, based on the echo data thus captured, an image is formed in predetermined time units (in units of frames or volumes). Processing with respect to the echo data is performed at a stage prior to or after the image formation, so that motion information representing a temporal change in the shape of the heart is obtained. In this case, for each frame data (or each tomographic image), an area of a portion of interest in the heart is calculated, to thereby measure the motion information indicating the changes of the area. It is also possible to process three-dimensional data to measure the temporal change in the volume as the motion information. Because the motion information is information indicating the change of the shape along the time axis, the periodical change in the motion information substantially corresponds to the periodical change of an electrical signal supplied to the heart (i.e. an electrocardiographic signal). As such, by analyzing the motion information, information equivalent to the information represented by an electrocardiographic signal can be obtained. According to the present invention, a specific time is determined from the motion information. Here, the specific time refers to a specific phase or a specific period in a cardiac cycle, such as end-diastole, end-systole, and so on. A synchronization signal indicative of the period of an R wave contained in an electrocardiographic signal can also be generated from the motion information.

As described above, according to the present invention, even in a situation where a fetal electrocardiographic signal cannot be observed directly, information equivalent to an electrocardiographic signal can be obtained by performing analysis of the ultrasonic data, especially analysis of the tissue motion, so that the information thus obtained can be displayed or the information can be used to compute further information. Conventionally, various measurements using an electrocardiographic signal from a fetus cannot be performed because an electrocardiographic signal cannot be obtained from a fetus. The above structure of the present invention makes it possible to perform such measurements even with regard to the fetal heart. In conjunction with the above structure, the time information may be obtained in real time while an ultrasonic image is being displayed, or the time information may be obtained by using echo data stored in a memory.

Preferably, the motion information is information representing a change in an area or a change in a volume concerning a portion of interest in the fetal heart. While the portion of interest is desirably a heart chamber in the fetal heart, it may be a cardiac muscle portion. The heart chamber may be a left ventricle, for example, and the temporal change in the area (area value) or the volume (volume value) concerning an entire heart chamber or a portion of the heart chamber may be observed.

Preferably, the motion information measurement section includes an extraction section for extracting, for each frame, a region corresponding to a portion of interest in the fetal heart based on echo data which is used for forming a tomographic image, the echo data having been obtained by transmission and reception of the ultrasound; an area calculation section for calculating an area concerning the region corresponding to the portion of interest for each frame; and a graph generation section for generating, as the motion information, a graph representing a temporal change in the area which is calculated for each frame.

Preferably, the time measurement section performs waveform analysis of the graph generated as the motion information to specify at least one of a maximum value and a minimum value as a peak for each heartbeat.

Preferably, the time measurement section includes a smoothing section for performing smoothing processing with respect to the graph serving as the motion information; and a peak specification section for specifying the peak for each heartbeat in a graph to which the smoothing processing has been performed. With this structure, because the peak can be specified after smoothing the waveform by the smoothing processing, the likelihood of the time measurement being effected by noise can be reduced, so that the accuracy of measurement can be increased. While the timing at which the maximum value occurs generally corresponds to the actual end-diastole (or end-systole), they may not correspond, depending on the portion measured. In such a case, correction with regard to time can be performed so as to establish a correspondence between the maximum value and the diastolic or systolic peak. However, when the cardiac cycle is simply being observed, such inconsistency of timing creates not disadvantage or problem.

Preferably, the peak specification section is an end-diastole specification section, and when a plurality of local maximum values are present on the graph, the end-diastole specification section specifies the maximum value among the plurality of local maximum values by using a determination window which is smaller than a standard cardiac period concerning a fetal heart. In order to increase the accuracy of time measurement, it is necessary to prevent misidentification of the maximal value and the minimum value. In this regard, it is preferable that the reference for detecting the maximum and minimum values is determined based on the standard cardiac cycle concerning the fetal heart. The determination window on the time axis is set as a time period which is shorter than the standard cardiac period, and this determination window is used to determine the range within which the maximum value in each heartbeat is searched. In this case, a plurality of time conditions may be used, or a determination condition of the maximum value or the like may be provided in the direction of the amplitude axis.

Preferably, the ultrasound diagnosis apparatus further includes a cardiac information calculation section for calculating cardiac information concerning the fetal heart based on the specific time which is measured. The cardiac information may include, for example, the heart rate per minute, the cardiac cycle (a time period of a single heartbeat), a degree of variation in these values (distribution), and so on. Preferably, the ultrasound diagnosis apparatus further includes an evaluation value calculation section for calculating an evaluation value for evaluating a function concerning the fetal heart based on the specific time which is measured. In general, the evaluation value may be a value obtained as a result of heart function measurement using an electrocardiographic signal or a cardiac synchronization signal. Preferably, the evaluation value is defined by a size of the left ventricle or a portion of the left ventricle at end-diastole and end-systole. A typical evaluation value may be an ejection fraction (EF).

Preferably, the ultrasound diagnosis apparatus further includes a display processing unit for displaying a graph which directly or indirectly represents the motion information and a mark indicative of the specific time on the graph. With this structure, correctness of the measurement concerning the specific time can be confirmed on the screen.

A method according to the present invention includes calculating an area of the left ventricle or a portion of the left ventricle in units of predetermined time based on echo data obtained by transmitting and receiving ultrasound with respect to a fetal heart and generating a graph representing a temporal change concerning the area of the left ventricle or a portion of the left ventricle; specifying a time phase of at least one of end-diastole and end-systole by performing waveform analysis with respect to the graph; and calculating at least one of a heart rate, a cardiac cycle, and a heart function evaluation value concerning the fetal heart, by using the time phase of at least one of end-diastole and end-systole which is specified. In the method, the echo data is processed to obtain time information corresponding to electrocardiographic information.

BRIEF DESCRIPTION OF THE DRAWINGS

A preferred embodiment of the present invention will be described in detail based on the following figures, wherein.

DETAILED DESCRIPTION

A preferred embodiment of the present invention will be described in detail with reference to the accompanying drawings.

Figure 1:
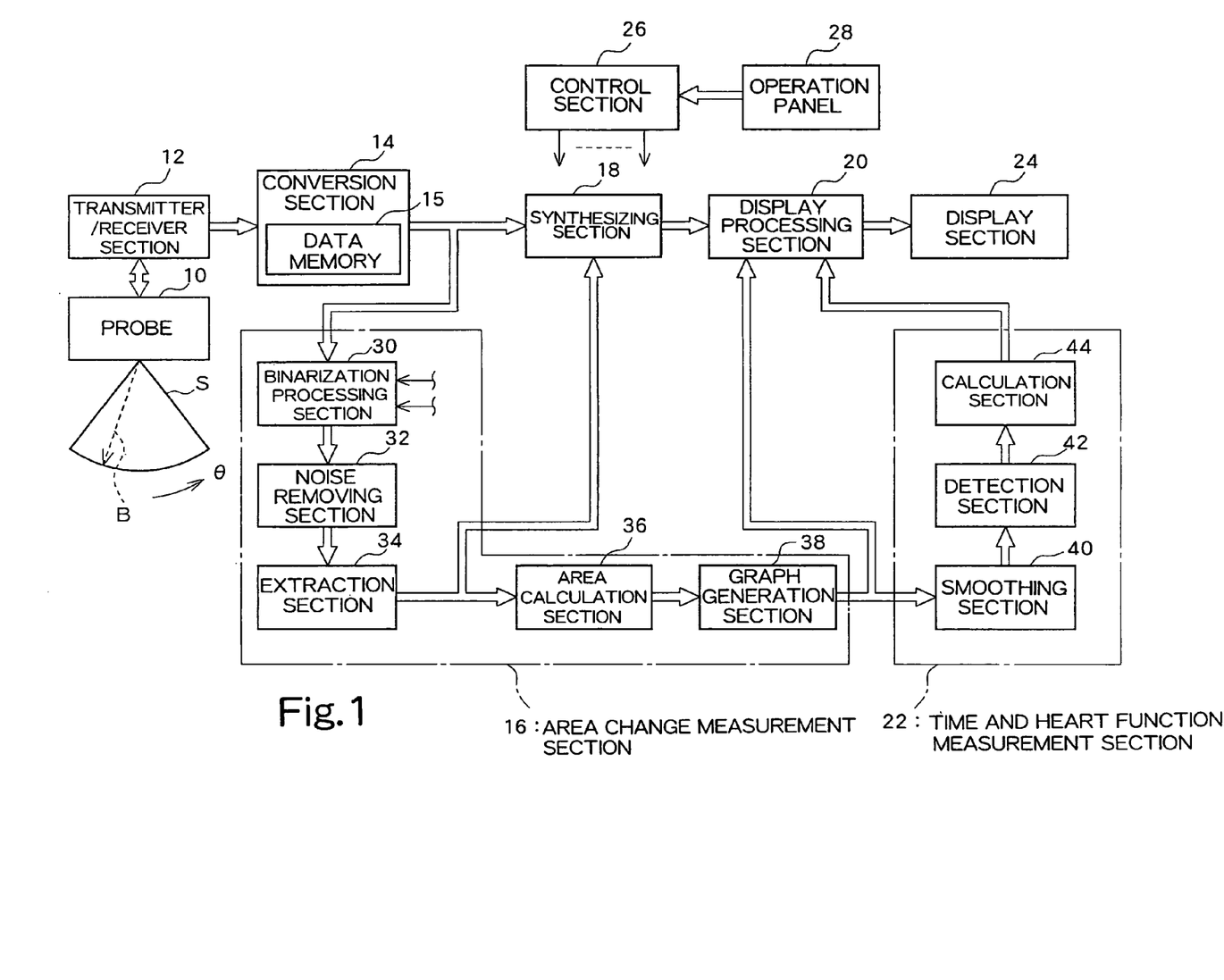
FIG. 1 is a block diagram showing an ultrasound diagnosis apparatus according to one embodiment of the present invention.

FIG. 1 shows an ultrasound diagnosis apparatus according to one embodiment of the present invention. Specifically, FIG. 1 is a block diagram showing an overall structure of an ultrasound diagnosis apparatus. The ultrasound diagnosis apparatus according to the present embodiment performs ultrasonic diagnosis concerning the heart in a living body, particularly concerning the heart of a fetus (a fetal heart), although the apparatus of the present embodiment can obviously also be used for ultrasonic diagnosis of a heart in a living body other than a fetus.

A probe 10 is a transmitter/receiver which transmits ultrasound pulse and receives reflected ultrasound to thereby form an ultrasound beam B. The probe 10 includes an array transducer formed of a plurality of transducer elements. The ultrasound beam B which is formed by the array transducer is electronically scanned. As electronic scanning methods, electronic sector scanning, electronic linear scanning, and so on are known. While in this embodiment, a 1D (one-dimensional) array transducer is provided in the probe 10, a 2D array transducer may be provided.

When the ultrasound beam B is electronically scanned, a scan plane S is formed as shown in FIG. 1. In FIG. 1, the electronic scanning direction is indicated as the θ direction. The scan plane S is a two-dimensional data acquisition region, and a tomographic image concerning the fetal heart is formed based on echo data on the scan plane, as will be described below. The scan plane S is formed repeatedly, so that a tomographic image is displayed on the display screen as a motion image. Under such conditions it is possible, according to the present embodiment, to obtain a synchronization signal (a pseudo electrocardiographic signal) equivalent to an electrocardiographic signal. In addition, such a synchronization signal can be obtained in real time, as will be described in detail below.

Here, the probe 10 is brought into contact with the abdomen of the fetus' mother. Alternatively, the probe 10 may be inserted into the mother's vagina. Other types of probe may also be used.

A transmitter/receiver section 12 functions as a transmitting beam former and a receiving beam former. The transmitter/receiver section 12 supplies a plurality of transmission signals to the array transducer where a transmitting beam is formed. Reflection waves from within the living body are received by the array transducer, which then transmits a plurality of reception signals to the transmitter/receiver section 12. The transmitter/receiver section 12 applies phase-alignment and summation processing to the plurality of reception signals, thereby electronically forming a receiving beam. The reception signal having been subjected to the phase-alignment and summation processing is output to a conversion section 14 via a signal processing section which is not shown.

In the present embodiment, the conversion section 14 is provided with a coordinate converting function, an interpolation processing function, and so on, and is formed by a digital scan converter (DSC). Through the processing of the conversion section 14, a tomographic image is formed based on the echo data on the scan plane S. The image data of the tomographic image is to be stored in a data memory 15. In the present embodiment, area calculation, time measurement, and so on is performed with respect to the image data having been subjected to coordinate conversion, as will be described below. However, area calculation, time measurement, and so on can also be applied to the image data prior to coordinate conversion. More specifically, the frame data which are subjects of calculation and measurement may be a group of beam data prior to coordinate conversion or image data after coordinate conversion, both of which corresponds to frame data. It is also possible to apply volume calculation or the like to volume data, rather than the frame data. The image data of each frame which is output from the data memory 15 is supplied to a synthesizing section 18 and is also supplied to an area change measurement section 16.

The synthesizing section 18 has a function of synthesizing, in frame units, the tomographic image and an image of a heart chamber which is formed by the area change measurement section 16 and generating a synthesized image. This synthesizing section 18 is provided, as required.

A display processing section 20 forms display screen data including the synthesized image described above, a graph image, and numeral information as a result of calculation, and outputs the data to a display section 24. The content of the display screen can be appropriately determined in accordance with a user request. A control section 26 performs operation control of each structure shown in FIG. 1, and an operation panel 28 is connected to the control section 26. The control panel 28 includes a keyboard, a trackball, and the like, and can be used by a user for setting a region of interest (ROI), inputting measurement conditions and operation mode, and so on.

The area change measurement section 16 will be described. The image data output from the conversion section 14 has been sent to a binarization processing section 30. The binarization processing section 30 is a module which executes, on the frame basis, binarization processing or two-point discrimination with respect to the image data. For example, the binarization processing section 30 executes chamber portion in the heart and allocating a pixel value "0" to other portions. In such a case, the threshold value required for the binarization processing can be variably set by a user through control of the control section 26. Further, it is possible to designate, as a region of interest, a subject of the binarization processing or a region to which extraction processing is to be applied, which will be described below, so that the binarization processing or the extraction processing is applied only within the region of interest. In this case, more than one region of interest can be designated. It is also possible to apply area calculation processing to a plurality of partial regions in parallel.

A noise removing section 32 executes noise removing processing with respect to the binary image formed by the binarization processing section 30. An extraction section 34 then executes processing for extracting the heart chamber in the binary image which has been subjected to noise removal. For example, the extraction section 34 can extract, as a closed region, the left ventricle included in the region of interest by repeatedly executing image processing including image expansion and image contraction. Here, it should be obvious that any heart chamber other than the left ventricle, i.e., the right ventricle, the right atrium, and the left atrium can also be extracted. With this extraction processing, the left ventricle, for example, is extracted as a specific portion of interest, and an image of the heart chamber representing the portion of interest is generated. The image data of the heart chamber image is supplied to the synthesizing section 18 and is also supplied to an area calculation section 36.

The area calculation section 36 calculates an area (an area value) concerning the heart chamber thus extracted. This area calculation is performed on a frame basis. Specifically, in a state where a series of heart chamber images are input in time sequence, the area of the heart chamber image in each frame is calculated. Consequently, a series of area data (area values) is generated in time sequence.

A graph generation section 38 generates a graph (an area graph or an area change graph) representing the series of area data obtained as described above on the time axis. This graph corresponds to image data which represents a temporal change in the area as a waveform. This image data is supplied to the display processing section 20 and is also output to a time and heart function measurement section 22. The above-described graph represents a temporal change of the shape of a specific region in the fetal heart. The graph can be considered to represent cardiac information of the fetus because the fetal heart periodically moves in accordance with an electrocardiograph signal. As such, while directly measuring an electrocardiographic signal from fetal heart is normally impossible or problematic, with the present invention a graph, that is motion information, can be obtained, so that temporal information concerning the fetal heart can be obtained by analyzing the waveform of the motion information, and, more particularly, a specific time can be determined. For this reason, the time and heart function measurement section 22 which will be described below is provided.

In the time and heart function measurement section 22, the image data which represents the above-descried graph is input to a smoothing section 40. The smoothing section 40 performs smoothing processing, that is, averaging processing, with regard to the image data. With this processing, noises that are present on the graph can be reduced, so that detection of the maximum value and detection of the minimum value which will be described below can be performed with high precision.

A detection section 42 applies a method which will be described in detail below to the graph which has been subjected to averaging, to thereby specify, as peaks, the maximum value and the minimum value of the waveform for each heartbeat. Here, when the heart chamber being subjected to area calculation is the left ventricle, it is determined that the maximum value corresponds to the time of the end-diastole and the minimum value corresponds to the time of end-systole. As such, the detection of the maximum value and the minimum value as described above enables detection of information indicative of a specific time, such as R wave which is obtained from an electrocardiographic signal. Here, while the period of the waveform of an actual electrocardiographic signal should be identical with the period of the waveform represented by the above-described graph, if times do not correspond to each other between these graphs, such a time difference may be eliminated by correction, or measurement and calculation may be performed in consideration of the time difference.

A calculation section 44 specifies the end-diastole and the end-systole from the times indicated by the maximum value and minimum value that are detected, and outputs the timing information indicative of the specified information to the display processing section 20. Further, the calculation section 44 specifies the time of the end-diastole for each heartbeat to thereby calculate the heart rate per minute, and outputs the heart rate to the display processing section 20. The calculation section 44 uses the similar method to further calculate the cardiac cycle and outputs the information to the display processing section 20. Here, it is also possible to sequentially observe the time of the end-systole to thereby calculate the cardiac information rather than sequentially observing the time of the end-diastole to calculate the cardiac information. Alternatively, two calculation results obtained by these two types of information can be compared and adjusted to thereby obtain the cardiac information with higher precision.

In the present embodiment, the calculation section 44 has a function of calculating the ejection fraction (EF) as an evaluation value for the heart functions. Conventionally, calculation of the ejection fraction through ultrasonic diagnosis of a fetal heart has been problematic because an electrocardiographic signal cannot be obtained. According to the present embodiment, however, the ejection fraction can be calculated in a simple manner by using the specified time phases and the results of area calculation described above. Here, the ejection fraction (EF) can be obtained from the operation "(area at the end-diastole (end-diastolic area)–area at the end-systole (end-systolic area))/area at the end-diastole (end-diastolic area)", for example. The volume can be used in place of the area. Further, as will be described below, it is also possible, when a plurality of partial regions are set within the heart chamber, to calculate the ejection fraction or the equivalent information for each partial region. The numeral value information indicative of the ejection fraction obtained by the calculation section 44 is output to the display processing section 20.

Figure 2:
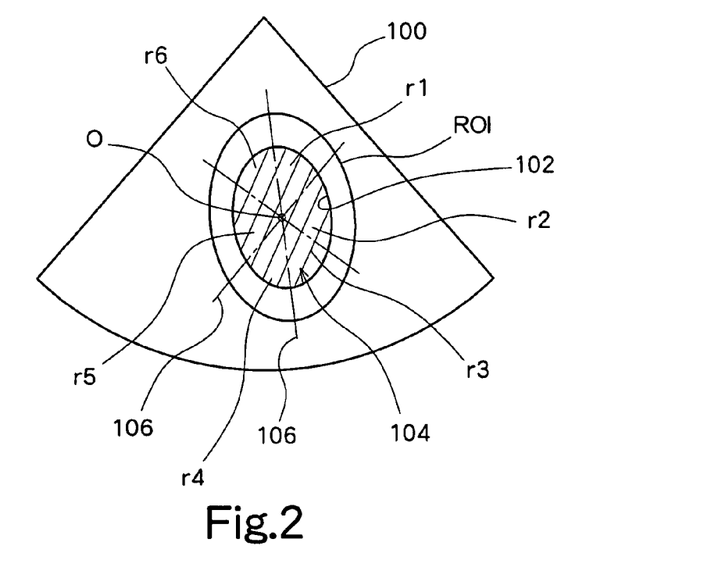
FIG. 2 is a view showing a region of interest which is set on a tomographic image.

FIG. 2 illustrates tomographic image data 100. More specifically, the illustrated tomographic image data 100 is binary data obtained after binarization processing. The region of interest (ROI) is set, by a user or automatically, so as to enclose the left ventricle 104 of a fetal heart, and the region indicated by the ROI is to be subjected to the extraction processing. As a valve is present within the heart and the valve moves periodically, there are cases where a closed region cannot be extracted. In order to deal with such cases, the ROI is set and the extraction operation is executed within the range of ROI, so that a problem that the extraction operation is dispersed can be prevented. Accordingly, when the closed region can reliably be extracted, it is not necessary to set the ROI. In FIG. 2, numeral 102 indicates endocardium, and the portion located internally with respect to the endocardium serving as a boundary is the fetal left ventricle 104 and the portion located externally with respect to the endocardium is cardiac muscle or other sites. In the drawing, other heart chamber such as the left atrium are not shown because these heart chambers are removed from the extraction subjects by setting the ROI.

As shown in FIG. 2, a center point O of the fetal left ventricle 104 is set, and a plurality of lines 106 extending radially from the center point 104 are also set, as required. Consequently, a plurality of regions (partial regions) r1 to r6 segmented by the plurality of lines 106 are defined, and area calculation can be performed for each partial region r1 to r6. For example, it is possible to generate the above-described graph concerning a region with a greater change in the area, or to form a plurality of graphs and then specify the time phase in heartbeat while comprehensively considering the graphical information.

Figure 3:
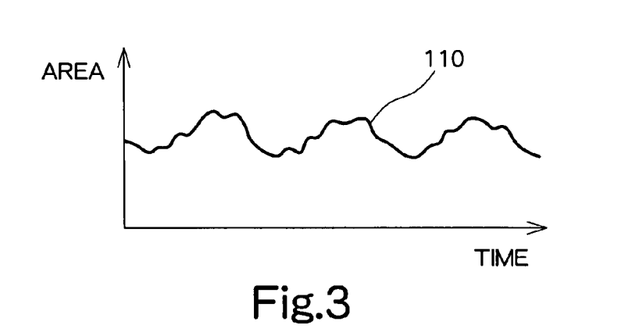
FIG. 3 is a graph showing a state prior to averaging processing.
Figure 4:
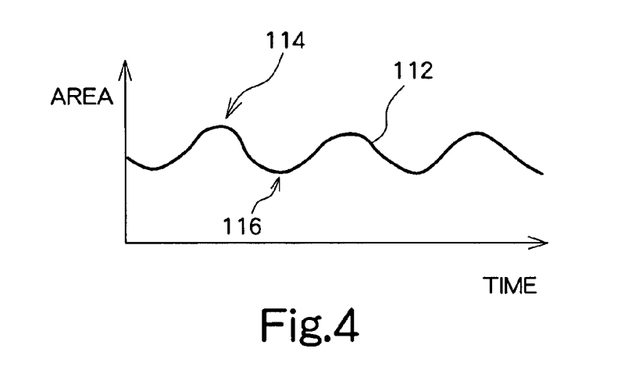
FIG. 4 is a graph showing a state after averaging processing.

With reference to FIGS. 3 and 4, the operation of the smoothing section 40 shown in FIG. 1 will be described. FIG.

3 shows a graph 110 which is generated by the graph generation section 38 shown in FIG. 1. In the graph 110, the horizontal axis is a time axis and the vertical axis indicates an area (an area value). In some cases, the graph 110 contains noise or ripple components as illustrated, and there is therefore a possibility that specification of times (time phases) cannot be performed precisely if the maximum and minimum values are detected with this state. Accordingly, the smoothing section 40 performs the averaging processing as shown in FIG. 4 prior to detection of the maximum and minimum values. More specifically, numeral 112 represents a graph after the averaging processing. When the waveform is observed after this averaging processing, three periods clearly appear along the time axis. Here, numeral 114 indicates the upper peak, that is, the maximum value, and numeral 116 indicates the lower peak, that is, the minimum value. The maximum value and the minimum value are specified for each heartbeat.

Here, there is a possibility, even with the averaging processing described above, of a plurality of local maximum values and a plurality of local minimum values appearing within each heartbeat. Therefore, according to the present embodiment, a time window for searching the local maximum and the local minimum on the time axis, that is, a time condition, is adopted. Such a time condition is determined using the heart rate of a standard fetus. Here, the heart rate of an average fetus is 110 per minute to 160 per minute. In general, a heart rate over 180 beats per minute is diagnosed as tachycardia, and a heart rate under 100 beats per minute is diagnosed as bradycardia. With conversion of the heart rate into the cardiac cycle, a standard cycle of a single heartbeat of a fetus is determined to be 400 to 500 msec. Therefore, a cycle under 330 msec is determined to be tachycardia and a cycle over 600 msec is determined to be bradycardia. As such, a normal cardiac cycle of a fetus can be considered to be 330 msec or more, for example. Specifically, by using, as a determination criteria, the time range shorter than this cycle which serves as one reference, the maximum value and the minimum value for each heartbeat can be precisely determined. While, in the method of the present embodiment which will be described below, the cycle of 300 msec is adopted as an example, it is desirable that the numeral be variably set depending on the situation. Further, when a plurality of time conditions are simultaneously applied, the determination of the maximum and minimum values can be accomplished with an even higher precision.

Figure 5:
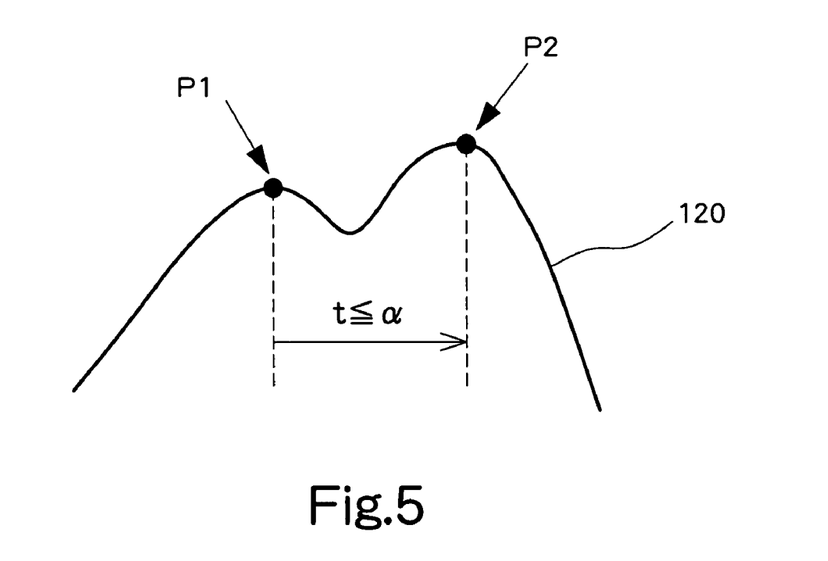
FIG. 5 is a view for explaining a method of specifying the maximal value among a plurality of local maximal values.
Figure 6:
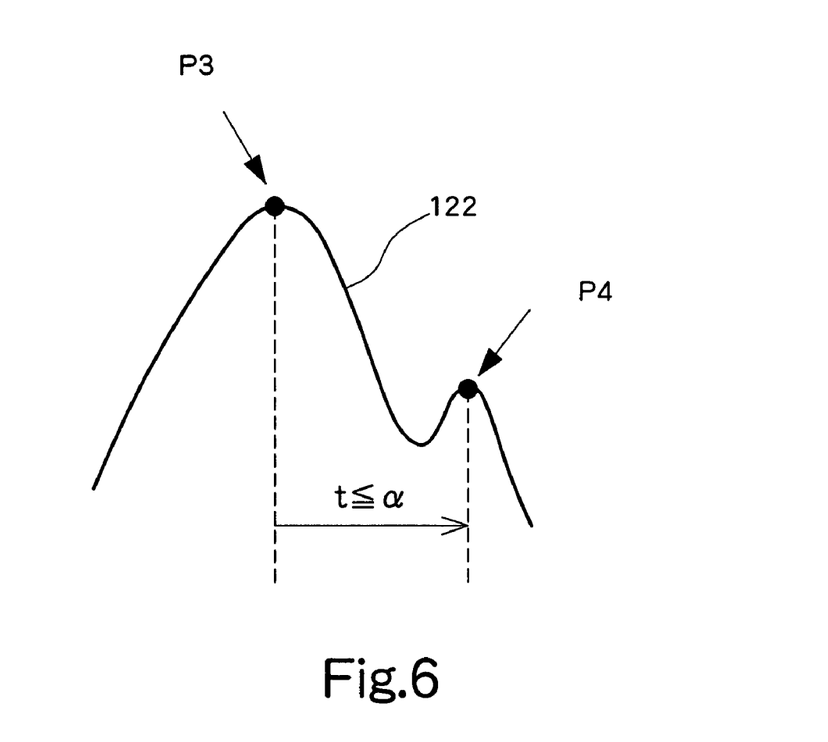
FIG. 6 is a view, which is similar to FIG. 5, for explaining a method of specifying the maximal value among a plurality of local maximal values.

FIGS. 5 and 6 illustrate a basic principle of the maximum value specification method, only as one example. When a plurality of local maximum values are present within a single heartbeat as shown in FIGS. 5 and 6, it is necessary to specify the maximum value among, these local maximum values. Accordingly, in the present embodiment, a time condition α is defined, and a time-period t between the local maximum detected immediately before the present time and the local maximum currently detected is compared with α. If the condition t≦α is satisfied, processing in which the temporary maximum value specified heretofore (a candidate maximum value) is updated is executed, while otherwise no such update processing is executed. When searching the maximum value, a can be set to 100 msec or 200 msec. For example, as shown in FIG. 5, when two local maximum values P1 and P2 are present on the graph 120 and P1 is first detected and then P2 is detected within a time range which satisfies the time condition t≦α, the values of P1 and P2 are compared. If P2 is greater than P1, P2 is determined to be the maximum value (candidate). In this case, if another local maximum is present after P2, it is possible to set a new time condition using P2 as a reference, and, in a state where the time condition is satisfied, to perform comparison once again. At this time, the time condition using P1 as a reference may be maintained. In the example shown in FIG. 6 in which two local maximum values P3 and P4 are present on the graph 122, while P4 satisfies a time condition which is defined using P3 as a reference, P4 is smaller than P3. Accordingly, P3 is maintained as the maximum value (candidate).

Figure 7:
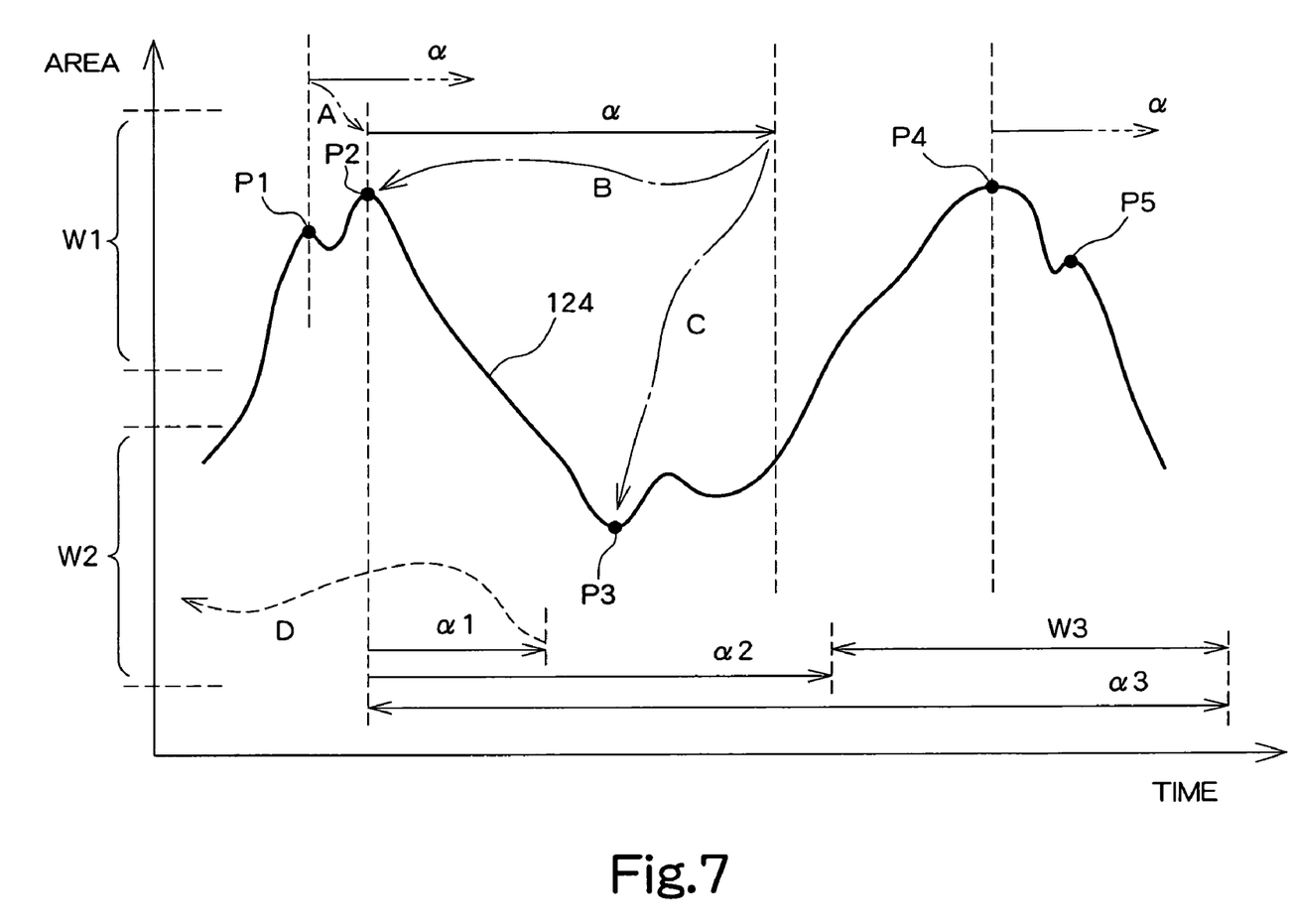
FIG. 7 is a view showing an example method for specifying the maximal value and the minimum value for each heartbeat.

FIG. 7 shows an example processing performed by the detection section 42 shown in FIG. 1. A local maximum value P1 is first detected on a graph 124, and a determination width α is first set using P1 as a reference. Then, as a local maximum value P2 which is detected the next is within the range α, the values of P1 and P2 are compared. In this example, because P2 is greater than P1, P2 is designated as a candidate of the maximum value. Then, the time width α is set once again, with P2 being used as a time reference (see A in FIG. 7). Here, the local maximum P1 which is detected first may be set as a fixed time reference.

After the maximum value candidate P2 is detected, a local maximum is searched for along the time axis direction along the graph 124. In the present embodiment, the search for a minimum value is executed in parallel with the search for the maximum value, and the smallest value of the values which have been referred at any point are always stored. In the example shown in FIG. 7, when no new candidate for the maximum value appears within the range of α with reference to the timing of P2, the local maximum P2 which was previously detected is confirmed to be the maximum value at the termination of the period α (see B in FIG. 7). At the same time, the local minimum value having the smallest value among the values detected until then is determined to be the minimum value. In the example shown in FIG. 7, the local minimum indicated as P3 constitutes the minimum value, and its value is specified as the minimum value (see C in FIG. 7). Here, for measurement of the heart rate and the cardiac cycle with regard to the fetal heart, it is sufficient to specify at least one of the minimum value and the maximum value, while, in the operation example which will be described below, only the time at which the maximum value appears is sequentially specified. More specifically, in that example, monitoring of the time at which the minimum value indicated by P3 appears is not performed. Nevertheless, if the time phase concerning the minimum value is additionally specified, more precise measurement can be achieved.

In the present embodiment, at a time point where the time period α elapses from a start point which is the local maximum P2 serving as the maximum value, the heart rate, the cardiac cycle, and the ejection fraction (EF) are calculated. Simultaneously, the maximum value, the minimum value, and the maximum value time (i.e. the end-diastole time) which have been detected until that time are temporarily cleared, and further search is resumed. More specifically, in the next heartbeat, a local maximum P4 which is the maximum value is specified. When a local maximum P5 is detected thereafter, the local maximum P5, whose value is smaller than P4, is disregarded.

It should be noted that the determination method shown in FIG. 7 is only an example, and various modifications can be considered. For example, as described above, it is possible to fixt the local maximum P1 which is detected first as a start timing for setting the time period α. Further, the time condition which is used for searching the maximum value and the time condition which is used for searching the minimum value may be set individually. It is also possible to define a comparatively short time range α1 using the timing of P2 as a reference, and, when the time period α1 terminates, to determine the maximum value P2 in the current heartbeat and also specify the minimum value in the previous heartbeat that appears prior to the maximum value P2 (see D in FIG. 7). When this is done, however, for calculation of the ejection fraction (EF), in each heartbeat, the maximum value and the minimum value appearing after the maximum value are used. Alternatively, with the timing of the maximum value in the previous heartbeat being used as a reference, the range for searching the maximum value in the following heartbeat may be determined. In such a case, the ranges α2 and α3 are determined, and the search for the maximum value may be performed within the time width W3 which is defined between these values. In addition, while in the above description the determination condition for the time information is illustrated, it may be desirable to additionally set the determination condition concerning the area, for example. For example, the width W1 can be set for determining whether or not the value detected as the maximum value is appropriate. Similarly, the width W2 can be set for determining whether or not the value detected as the minimum value is appropriate. In this regard, a condition may also be set for determining whether or not the ejection fraction which is finally calculated falls within an appropriate range.

Regardless of the configuration employed, it is always desirable that waveform analysis be performed in such a manner that the maximum value and the minimum value in each heartbeat can be precisely specified on the graph. It is further desirable that the maximum value and the minimum value for each heartbeat which are thus specified are used to calculate the evaluation value for heart function. Here, it is advantageous that erroneous determination in specifying the maximum value and the minimum value can be prevented by defining the determination conditions for the maximum value and the minimum value based on average or standard cardiac cycle and peak values for a fetal heart.

Figure 8:
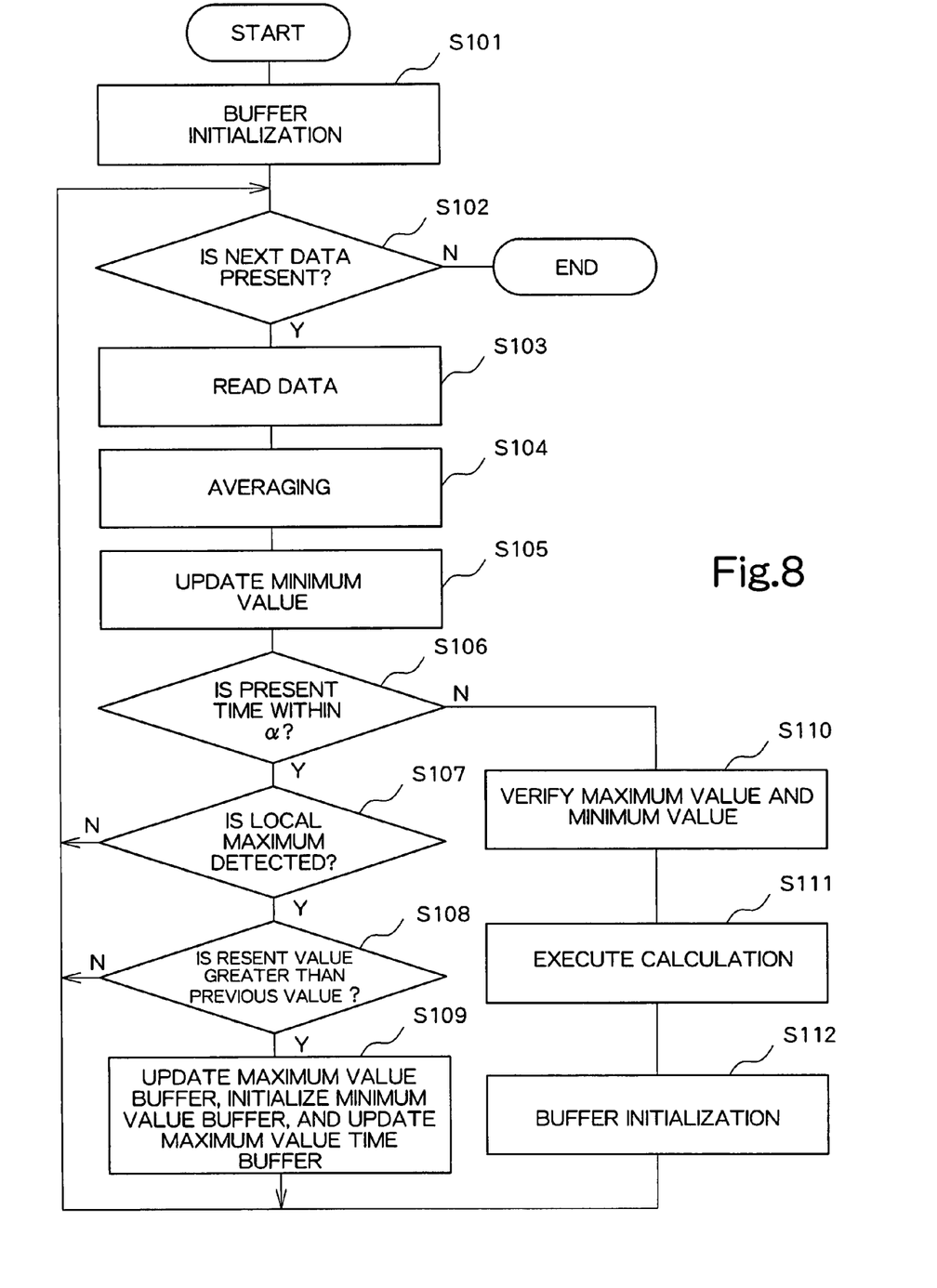
FIG. 8 is a flowchart showing an example operation of a time and heart function measurement section which is shown in FIG. 1.

The flowchart in FIG. 8 illustrates an example operation of the time and heart function measurement section 22 shown in FIG. 1. The flowchart shown in FIG. 8 illustrates an example method for executing the waveform processing shown in FIG. 7. In step S101, initialization with respect to buffers is performed. In the present embodiment, three buffers, that is, a maximum value buffer, a minimum value buffer, and a maximum value time buffer, are provided. With initialization of the maximum value buffer and the maximum value time buffer, 0 is written as a content of the respective buffers. With initialization of the minimum value buffer, a maximum buffer value is provided. It is a matter of course that various methods may be used for the initialization.

In step S102, when reading the waveform data of the graph generated by the area change measurement section 16 shown in FIG. 1, it is determined whether or not a next set of data is present and, if next data does not exist, this processing is terminated. If the next data is present, on the other hand, the process in step S103 is executed. In step S103, an amount of the waveform data corresponding to one point is read. Then, in step S104, the averaging processing with respect to the waveform data thus read is performed. This averaging processing is moving average processing, for example, in which filtering is performed along the time axis direction so that smoothing with respect to the waveform can be achieved. This processing corresponds to the function of the smoothing section 40 shown in FIG. 1.

The processes in step S105 and the subsequent steps indicate an example operation of the detection section 42 and the calculation section 44. In step S105, processing for updating the minimum value is executed. More specifically, the value which is currently being referred to and the value stored in the minimum value buffer are compared with each other, and, if the former is smaller, processing for writing this value in the minimum buffer is performed. With this processing, the smallest value is always stored in the minimum value buffer after initialization.

In step S106, whether or not a time condition is satisfied is determined. More specifically, whether or not the current time is within a period α from the time of appearance of the local maximum which is first detected. When the previous local maximum is not detected, this condition is always determined to be satisfied. In step S107, whether or not the value which is currently being referred to is a local maximum. For example, it is possible to detect a local maximum by obtaining a differential value of the waveform. It the value is not a local maximum value, the above-described processes in step S102 and the following steps are repeated.

When, on the other hand, it is determined in step S107 that the value which is currently being referred to is a local maximum, the local maximum value which was previously detected and the local maximum value which is currently detected are compared. If the former is greater than the latter, the process proceeds to step S102, whereas if the latter is greater than the former, the process proceeds to step S109.

In step S109, it is assumed that the local maximum value as a candidate of the maximum value is detected, the content of the maximum value buffer is updated. Specifically, the value of the local maximum newly detected is stored in the maximum value buffer. Further, the content of the minimum value buffer is initialized. Specifically, a largest buffer value is stored in the minimum value buffer, thereby clearing the value which is previously stored. In addition, the content of the maximum value time buffer is updated. Here, the maximum value time buffer, which is a buffer storing the time information in the present embodiment, may be configured to function as a timer. In such a case, in step S109, the maximum value time buffer is initialized, and more specifically, the count value is cleared. Thereafter, the processes in step S102 and the subsequent steps are executed.

On the other hand, when it is determined, in step S106, that the time condition is not satisfied, that is, when it is determined that the current time point is beyond the range of α from the time of appearance of the local maximum previously detected, in step S110, the values stored in the maximum value buffer and the minimum value buffer at that time point are confirmed, and then the contents are verified. More specifically, whether or not the two values respectively stored in the two buffers are within an optimal range is determined, and if they are within the optimal range, these values are to be used in the calculation in the following step S111. If any error is found in these values, error processing is performed. Here, it is also possible to additionally determine whether or not the heart rate, the cardiac cycle, and the ejection fraction are within an optimal range, so that generation of an error can be automatically recognized.

In step S111, the heart rate and the cardiac cycle are calculated as cardiac information from the time intervals of a plurality of maximum values which have been detected until the present time. In this case, it is also possible to calculate such information from the time intervals of a plurality of minimum values which have been detected until the present time. Further, the end-diastolic area serving as the maximum value and the end-systolic area serving as the minimum value are used to calculate the ejection fraction. In step S112, the content of all buffers is initialized, and the above-described processing is repeated in a similar manner with regard to the next heartbeat. The flowchart shown in FIG. 8 is only an example, and a variety of algorithms can be adopted as long as the maximum value and the minimum value can be appropriately determined for each heartbeat.

Figure 9:
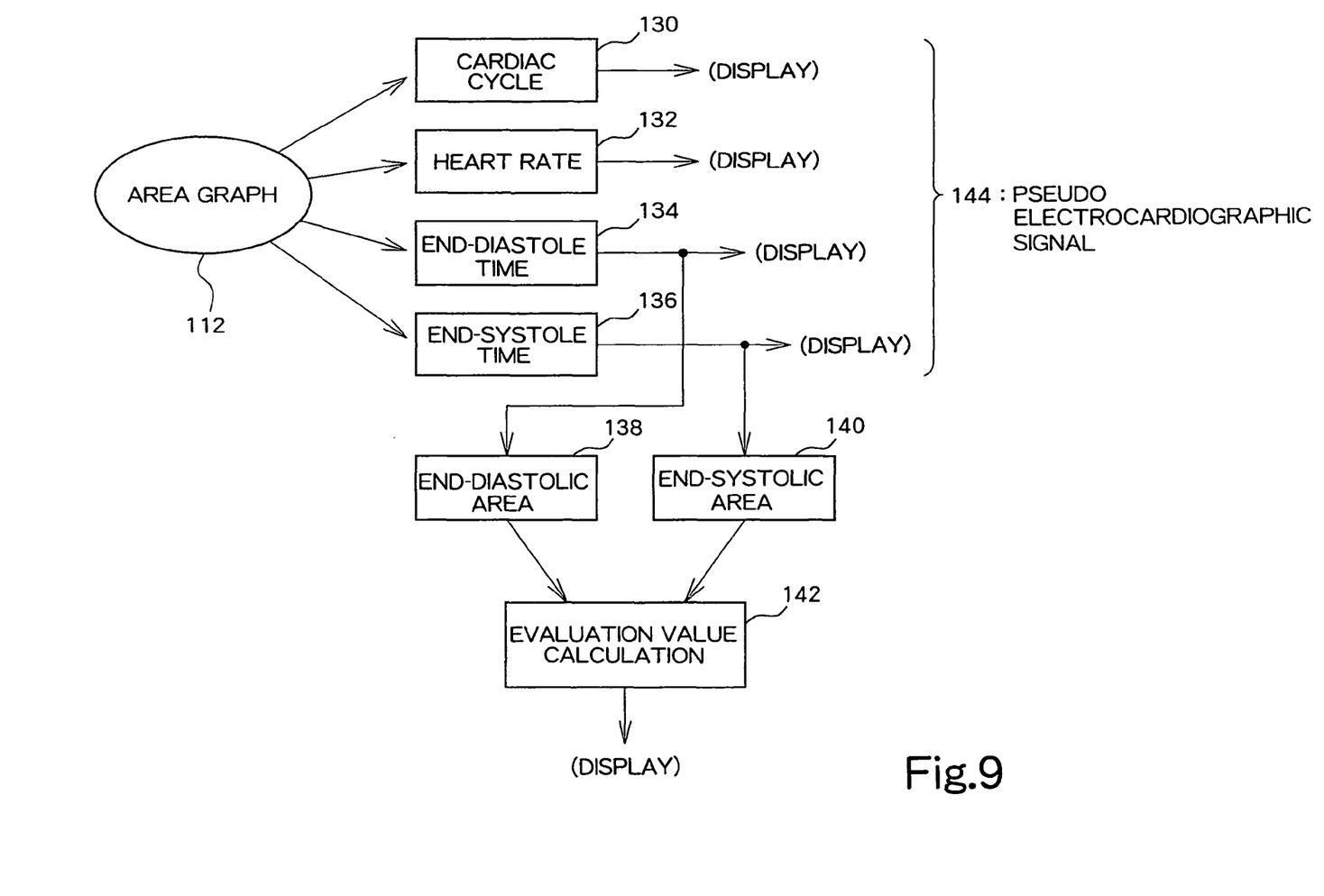
FIG. 9 is a conceptual view for explaining information obtained by the time and heart function measurement section.

FIG. 9 conceptually shows the content of processing performed by the time and heart function measurement section 22 shown in FIG. 1. As described above, the cardiac cycle 130 and the heart rate 132 are specified as cardiac information from the graph 112 which represents a change of area, and such information is displayed. Furthermore, on the basis of the graph 112, the end-diastole time 134 and the end-systole time 136 are specified, and displayed as required. Simultaneously, based on the end-diastolic area (the maximum value) 138 and the end-systolic area (the minimum value) 140 specified at the respective times, the ejection fraction serving as an evaluation value is calculated as indicated by numeral 142, and the calculation result is displayed. Here, each of the cardiac cycle 130, the heart rate 132, the end-diastole time 134, and the end-systole time 136 can be considered as a pseudo-electrocardiographic signal 144, that is, as an alternative to an electrocardiographic signal.

Figure 10:
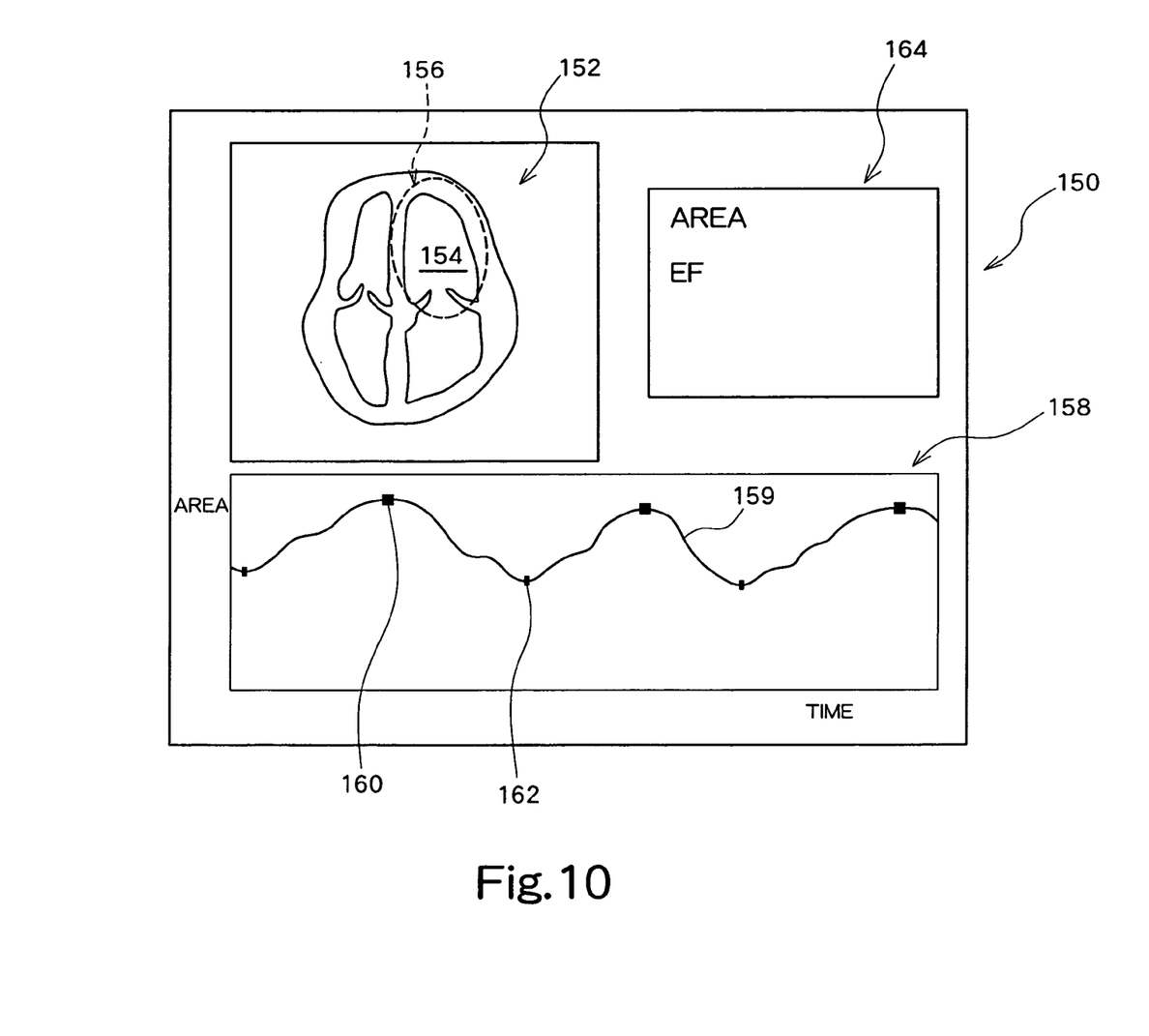
FIG. 10 is a view showing an example image displayed on the display section.

FIG. 10 shows an example display content which is displayed on the display section. Within a display screen 150, a tomographic image 152 is displayed. The tomographic image 152 represents a cross section of the left ventricle 154, and a region of interest 156 is set so as to enclose the left ventricle 154. A change in the area related to the left ventricle is represented by a waveform image 158. Specifically, the waveform image 158 includes a graph 159 in which a marker 160 indicative of the maximum value and a marker 162 indicative of the minimum value are displayed for each heartbeat. The markers are displayed using different shapes or different colors to enable the user to identify marker information and easily recognize the end-diastole time and the end-systole time for each heartbeat. Further, by monitoring such information, it is possible to confirm whether automatic calculation is being performed in an optimal manner.

The calculation result is displayed on the display screen 150 as numeral information 164. In the present embodiment, the area which continually changes is displayed using numerical values, and the ejection fraction (EF) which is calculated for each heartbeat is also displayed by numerical values. Naturally, a graph indicating a change of the ejection fraction can also be displayed in addition to the graph 159 indicating the change in the area.

Figure 11:
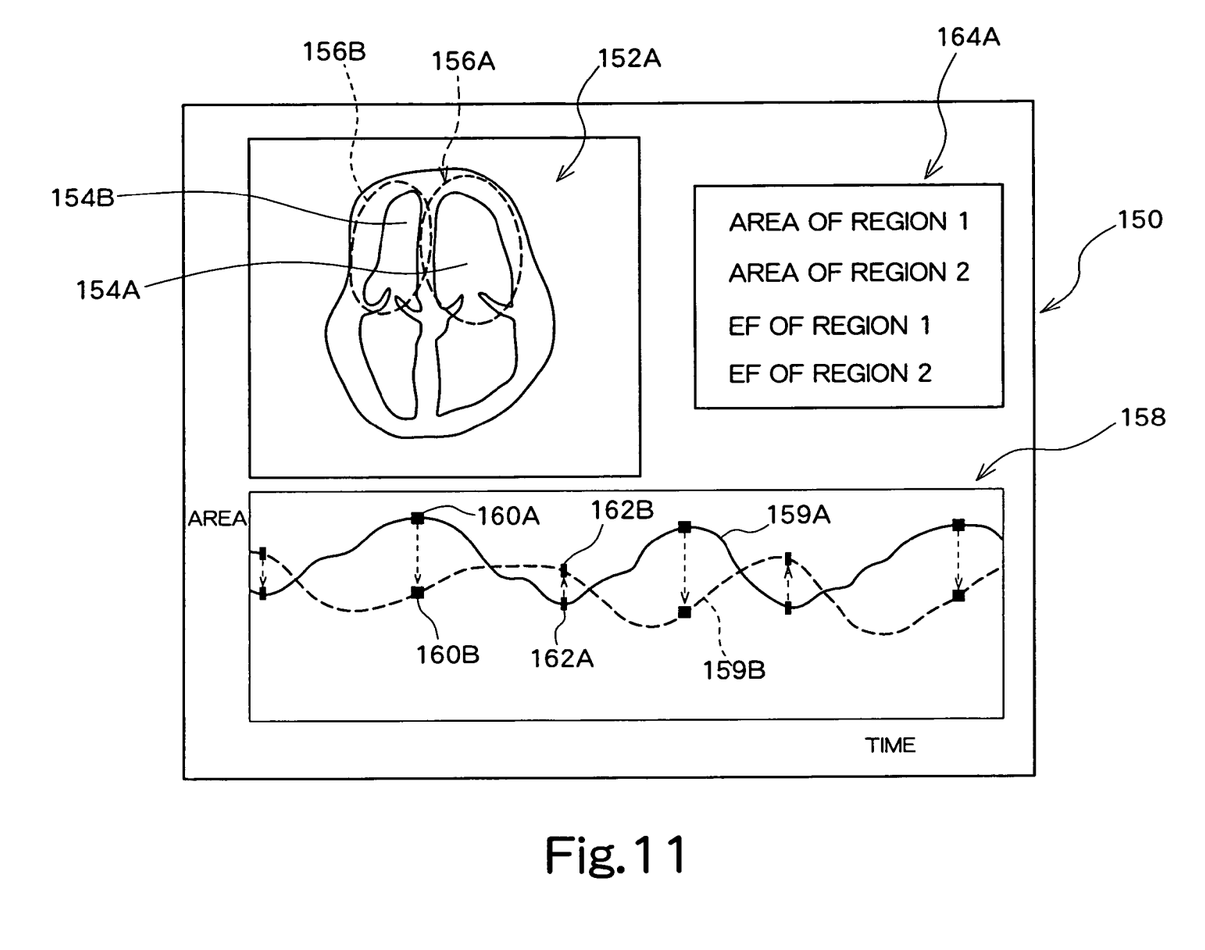
FIG. 11 is a view showing another example image displayed on the display section.

FIG. 11 shows another display example, in which a tomographic image 152A, a waveform image 158, and numeral display 164A are displayed on the display screen 150. In the tomographic image 152A, regions of interest 156A and 156B are set concerning the left ventricle 154A and the right ventricle 154B, respectively, and the area change is observed for each heart chamber. Accordingly, two graphs 159A and 159B are shown in the waveform image 158, representing the area change of the left ventricle and the area change of the right ventricle, respectively. On the respective graphs 159A and 159B, markers 160A and 160B indicative of the maximum values and markers 162A and 162B indicative of the minimum values are shown. In the example shown in FIG. 11, the times on the graph 159B representing the area change of the right ventricle are specified with reference to the graph 159A representing the area change of the left ventricle, so that the times indicated by the markers correspond to each other between the two graphs.

Figure 12:
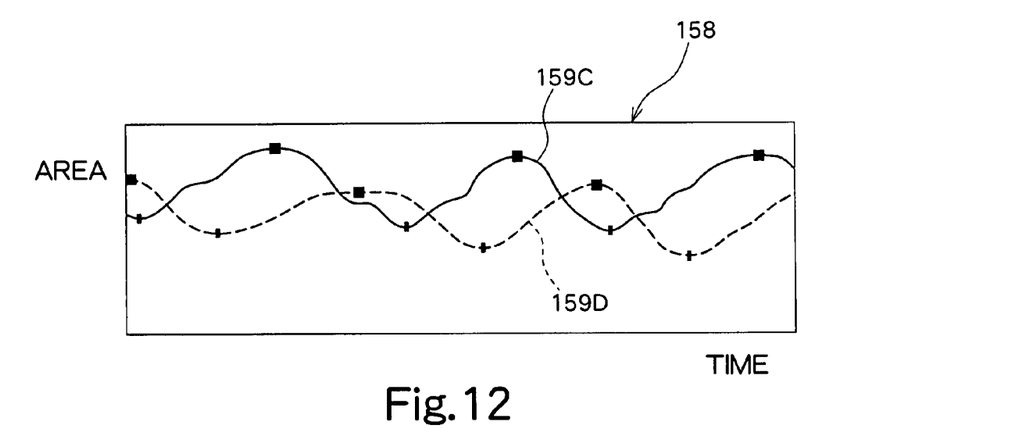
FIG. 12 is a view showing another example waveform image.

Naturally, in place of the above structure, a structure may be adopted in which the maximum value and the minimum value are detected independently on each graph 159C, 159D in the waveform image 158, and the corresponding markers are displayed, as shown in FIG. 12.

Figure 13:
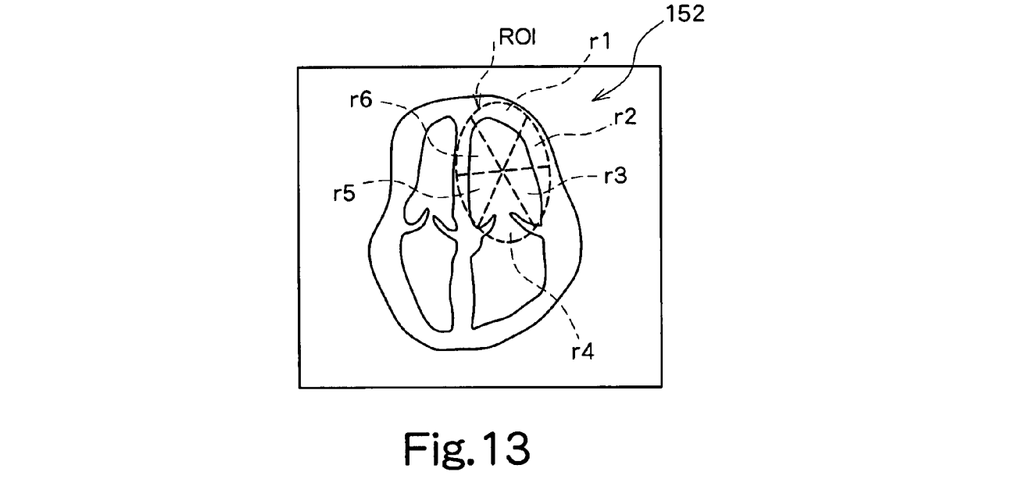
FIG. 13 is a view for explaining a region of interest which is segmented into a plurality of partial regions.
Figure 14:
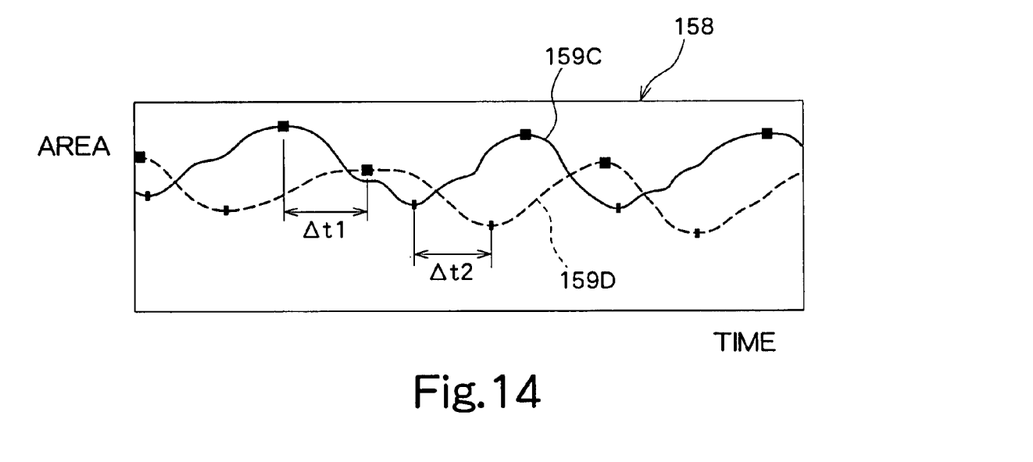
FIG. 14 is a view for explaining a time difference between two graphs.

FIG. 13 shows another example of setting of a region of interest. Specifically, in the tomographic image 152, an ROI is set so as to enclose the left ventricle, and the internal portion of the ROI is segmented into a plurality of regions r1 to r6. An area change in each region may be represented in a graph. Further, as shown in FIG. 14, the time difference between the graph 159C representing an area change of the left ventricle and the graph 159D representing an area change of the right ventricle, for example, may be displayed. In such a case, the time difference $\Delta t1$ between the maximum values specified in the respective graphs and the time difference $\Delta t2$ between the minimum values specified in the respective graphs may be measured independently. It is well known that in the heart various sites moves at different timings, and a difference in the timings may be indicative of a degree of damage or illness. Accordingly, with quantification of the difference in timings as described above, it is possible to provide a user with information which is useful for diagnosis of disorders or diseases.

As described above, with the ultrasound diagnosis apparatus in accordance with the present embodiment, it is possible to generate information equivalent to an electrocardiographic signal, which cannot be conventionally observed, on the basis of a tomographic image for each frame, and further to evaluate the heart functions while obtaining such information in real time. Thus, various measurements concerning the fetal heart which cannot be performed in the conventional ultrasonic diagnosis can now be achieved. As such, the present invention advantageously provides an ultrasound diagnosis apparatus which is useful for confirming healthfulness and diagnosing a disease concerning the heart of a fetus.

While the preferred embodiment of the present invention has been described using specific terms, such description is for illustrative purposes only, and it is to be understood that changes and variations may be made without departing from the spirit or scope of the appended claims.

What is claimed is:

1. An ultrasound diagnosis apparatus, comprising:
  a transmitter/receiver section for transmitting and receiving ultrasound with respect to a fetal heart;
  a motion information measurement section for measuring motion information representing a temporal change of a shape of the heart caused by periodical motion of the fetal heart, based on data obtained by transmission and reception of the ultrasound; and
  a time measurement section for measuring a specific time in the periodical motion of the fetal heart based on the motion information,
  wherein the motion information measurement section includes:
  an extraction section for extracting, for each frame, a region corresponding to a portion of interest in the fetal heart based on echo data which is used for forming a tomographic image, the echo data having been obtained by transmission and reception of the ultrasound;
  an area calculation section for calculating an area concerning the region corresponding to the portion of interest for each frame;
  a graph generation section for generating, as the motion information, a graph representing a temporal change in the area which is calculated for each frame; and
  a peak specification section for performing waveform analysis of the graph generated as the motion information to specify a peak for each heartbeat, wherein the peak corresponds to the specific time,
  wherein, when a plurality of local maximum values are present on the graph, the peak specification section specifies the peak among the plurality of local maximum values by using a determination window which is smaller than a standard cardiac period concerning the fetal heart, wherein the plurality of local maximum values include a first local maximum value P1 and a second local maximum value P2 which is detected next to the first local maximum value P1, wherein the peak specification section:

(a) sets the determination window to be after the first local maximum value P1;

(b1) when the second local maximum value P2 is not detected within the set determination window, determines that the first local maximum value P1 is the peak; and (b2) when the second local maximum value P2 is detected within the set determination window, compares the first local maximum value P1 and the second local maximum value P2 to thereby determine the peak.

2. The ultrasound diagnosis apparatus according to claim 1, further comprising:

a cardiac information calculation section for calculating cardiac information concerning the fetal heart based on the specific time which is measured.

3. The ultrasound diagnosis apparatus according to claim 1, further comprising:

a display processing unit for displaying a graph which directly or indirectly represents the motion information and a mark indicative of the specific time on the graph.

4. The ultrasound diagnosis apparatus according to claim 1, further comprising:

an evaluation value calculation section for calculating an evaluation value for evaluating a function concerning the fetal heart based on the specific time which is measured.

5. The ultrasound diagnosis apparatus according to claim 4, wherein the evaluation value is defined by a size of the left ventricle or a portion of the left ventricle at end-diastole and end-systole.

6. The ultrasound diagnosis apparatus according to claim 1, wherein the peak specification section performs waveform analysis of the graph generated as the motion information to specify at least one of a maximum value and a minimum value as the peak for each heartbeat.

7. The ultrasound diagnosis apparatus according to claim 6, wherein the time measurement section includes a smoothing section for performing smoothing processing with respect to the graph serving as the motion information, and the peak specification section specifies the peak for each heartbeat in a graph to which the smoothing processing has been performed.

8. The ultrasound diagnosis apparatus according to claim 7, wherein the peak specification section is an end-diastole specification section.

9. A method of processing echo data in an ultrasound diagnosis apparatus, comprising:

calculating the area of the left ventricle or a portion of the left ventricle in units of predetermined time based on echo data obtained by transmitting and receiving ultrasound with respect to a fetal heart and generating a graph representing a temporal change concerning the area of the left ventricle or a portion of the left ventricle;

specifying a time phase of at least one of end-diastole and end-systole by performing waveform analysis with respect to the graph; and calculating at least one of a heart rate, a cardiac cycle, and a heart function evaluation value concerning the fetal heart, by using the time phase of at least one of a specified end-diastole and end-systole, wherein when a plurality of local maximum values are present on the graph, the step of specifying a time phase comprises specifying a peak corresponding to the time phase among the plurality of local maximum values by using a determination window which is smaller than a standard cardiac period concerning the fetal heart, wherein the plurality of local maximum values include a first local maximum value P1 and a second local maximum value P2 which is detected next to the first local maximum value P1, wherein the specifying a peak comprises:

(a) setting the determination window to be after the first local maximum value P1;

(b1) determining that the first local maximum value P1 is the peak when the second local maximum value P2 is not detected within the set determination window; and (b2) comparing the first local maximum value P1 and the second local maximum value P2 to thereby determine the peak when the second local maximum value P2 is detected within the set determination window, wherein the echo data is processed to obtain time information corresponding to electrocardiographic information.

* * * * *